United States Patent
Nudd et al.

(10) Patent No.: US 11,599,830 B1
(45) Date of Patent: Mar. 7, 2023

(54) AUTOMATIC CHANGE IN CONDITION MONITORING BY PASSIVE SENSOR MONITORING AND MACHINE LEARNING

(71) Applicant: ClearCare, Inc., San Francisco, CA (US)

(72) Inventors: Geoffrey Nudd, San Francisco, CA (US); David Cristman, San Francisco, CA (US); Jonathan J. Hull, San Carlos, CA (US)

( * ) Notice: Subject to any disclaimer, the term of this patent is extended or adjusted under 35 U.S.C. 154(b) by 233 days.

(21) Appl. No.: 16/863,378

(22) Filed: Apr. 30, 2020

Related U.S. Application Data
(60) Provisional application No. 62/841,591, filed on May 1, 2019.

(51) Int. Cl.
| | |
|---|---|
| G06N 20/00 | (2019.01) |
| G08B 23/00 | (2006.01) |
| G16H 10/20 | (2018.01) |
| G06K 9/62 | (2022.01) |

(52) U.S. Cl.
CPC ........... *G06N 20/00* (2019.01); *G06K 9/6256* (2013.01); *G08B 23/00* (2013.01); *G16H 10/20* (2018.01)

(58) Field of Classification Search
CPC ...... G06N 20/00; G06K 9/6256; G08B 23/00; G16H 10/20
See application file for complete search history.

(56) References Cited

U.S. PATENT DOCUMENTS

| | | | |
|---|---|---|---|
| 11,195,616 B1* | 12/2021 | Seemakurty | G06N 5/003 |
| 2006/0001545 A1* | 1/2006 | Wolf | G08B 21/0446 340/686.1 |
| 2009/0315719 A1* | 12/2009 | Song | G08B 21/0446 340/669 |
| 2011/0245629 A1* | 10/2011 | Giftakis | A61B 5/1116 600/301 |
| 2012/0154582 A1* | 6/2012 | Johnson | G16H 40/20 340/521 |
| 2015/0206409 A1* | 7/2015 | Visvanathan | G08B 21/0446 340/573.1 |
| 2016/0147959 A1* | 5/2016 | Mariottini | G16H 50/20 706/46 |
| 2016/0210838 A1* | 7/2016 | Yan | G08B 25/001 |
| 2016/0256080 A1* | 9/2016 | Shen | A61B 5/6891 |
| 2016/0275776 A1* | 9/2016 | Shen | A61B 5/024 |
| 2016/0377704 A1* | 12/2016 | Harash | G01S 13/0209 342/21 |

(Continued)

OTHER PUBLICATIONS

Salamon, Justin et al., "A Dataset and Taxonomy for Urban Sound Research", Proceedings—22nd ACM International Conference on Multimedia, Nov. 2014, 4 pgs.

(Continued)

*Primary Examiner* — Curtis J King

(57) ABSTRACT

A machine learning system passively monitors sensor data from the living space of a patient. The sensor data may include audio data. Audio features are generated. A trained machine learning model is used to detect a change in condition. In some implementations, the machine learning model is trained in a learning phase based on training data that includes questionnaires completed by caregivers and identified audio features.

11 Claims, 13 Drawing Sheets
(2 of 13 Drawing Sheet(s) Filed in Color)

(56) References Cited

U.S. PATENT DOCUMENTS

| | | | |
|---|---|---|---|
| 2016/0379462 A1* | 12/2016 | Zack | G08B 21/0469 |
| | | | 340/539.12 |
| 2017/0268924 A1* | 9/2017 | Shin | G01V 8/10 |
| 2017/0277962 A1* | 9/2017 | Kudo | G16H 40/67 |
| 2018/0306609 A1* | 10/2018 | Agarwal | H04L 67/12 |
| 2018/0333083 A1* | 11/2018 | Orellano | G16H 50/30 |
| 2019/0108740 A1* | 4/2019 | Coke | G01S 7/415 |
| 2019/0140911 A1* | 5/2019 | Jain | G06N 5/003 |
| 2019/0147722 A1* | 5/2019 | Devdas | G08B 21/0461 |
| | | | 340/539.13 |
| 2019/0192753 A1* | 6/2019 | Liu | A61M 60/135 |
| 2019/0326020 A1* | 10/2019 | Woodward | G16H 80/00 |
| 2020/0151519 A1* | 5/2020 | Anushiravani | G06K 9/6269 |
| 2020/0163590 A1* | 5/2020 | Lin | A61B 5/7264 |
| 2020/0349347 A1* | 11/2020 | Morzhakov | G06V 10/34 |
| 2020/0359913 A1* | 11/2020 | Ghodrati | A61B 5/1117 |
| 2021/0142643 A1* | 5/2021 | Susna | A61B 5/7264 |
| 2021/0158965 A1* | 5/2021 | Receveur | G16H 50/20 |
| 2021/0160709 A1* | 5/2021 | Marumo | H04W 24/02 |
| 2021/0304007 A1* | 9/2021 | Pasupuleti | A61B 5/7246 |
| 2021/0398677 A1* | 12/2021 | Lanius | G06N 20/00 |

OTHER PUBLICATIONS

Dean, Katie M. et al., "Preliminary Data on a Care Coordination Program for Home Care Recipients", Journal of the American Geriatrics Society, vol. 64, No. 9, Sep. 2016, 4 pgs.

Davix, Ascar et al., "Fourier Spectrum Features for Face Recognition", International Journal of Innovative Technology and Exploring Engineering, vol. 9, Issue 4, Feb. 2020, 5 pgs.

* cited by examiner

AUTOMATIC CHANGE IN CONDITION MONITORING BY PASSIVE SENSOR MONITORING AND MACHINE LEARNING

CROSS-REFERENCE TO RELATED APPLICATIONS

This application claims priority to U.S. Provisional Application Ser. No. 62/841,591, titled "Automatic Change in Condition Monitoring and Alerting by Passive Audio Processing and Machine Learning", filed May 1, 2019, which is hereby incorporated herein in its entirety by this reference.

TECHNICAL FIELD

The present disclosure is related to monitoring health-related conditions of senior citizens and detecting changes in health-related conditions.

BACKGROUND

The health of senior citizens changes over time. In some cases, hospitalization and critical care can be avoided if a change in a health-related condition is detected early.

Research has shown, for example, that daily manual reporting of changes in condition with a standardized diagnostic questionnaire can aid in early detection of problems such as foot injuries in diabetes. In this approach, a caregiver typically answers a standardized set of questions at the end of each shift. The questionnaire has a standardized set of questions and answers that correspond to health conditions. Early detection means, for example, that patients can sometimes be seen and treated by a nurse rather than with a hospitalization later in time. (See, e.g., K. M. Dean, L. A. Hatfield, A. B. Jena, D. Christman, M. Flair, K. Kator, G. Nudd, and D. C. Grabowski, "Preliminary Data On A Care Coordination Program For Home Care Recipients," Journal of the American Geriatrics Society, v. 64, no. 9, September 2016, 1900-1903). This approach works well but can be difficult to maintain over time for a variety of reasons.

Consider, for example, some of the practical problems in implementing daily diagnostic questionnaires in a reproducible manner in an assisted care living situation. In assisted care living situations, a patient (typically a senior) may be assigned a caregiver who stops by a patient's home a certain number of times per week. Caregiver turnover can be high, which can result in new caregivers having to come up to speed on a variety of different procedures. Caregiver turnover also makes it more difficult for caregivers to spot changes in conditions over previous visits. For example, if Bob takes care of a senior for 4 months, then at the end of 4 months he is able to easily answer questions in a questionnaire about changes in appetite of the senior compared with previous visits. But if there is turnover and Sue takes over the caregiving, then in Sue's first few visits she may find it difficult to determine if the senior had a change in appetite and may also be unfamiliar regarding how to answer the questionnaire.

Questionnaires can also become overly repetitive, which means that over the course of months or years a caregiver may become bored and not apply sufficient attention to detail in filling out a standardized questionnaire.

Another problem is that the caregiver is typically not present the entire day. For example, in some assisted living situations, a caregiver may be present with the senior for a certain number of hours each day and a certain number of days per week. For example, suppose a caregiver takes care of a senior for three hours in the morning. After the caregiver has left for the day, the senior could experience a change in condition that might not be detected until the next visit by the caregiver. But some senior citizens can have changes in condition, such as falls, when a caregiver is not present.

SUMMARY

An apparatus, system, and method are disclosed in which there is passive monitoring of at least one sensor input from a patient's living space. In some implementations, the sensor input may include an audio input. However, more generally the sensor input may include one or more of an audio input, a camera input, a video input, and a motion sensor input. A machine learning system monitors the at least one sensor input. In response to detecting a change in condition, the machine learning system generates a notification of the change of condition. In some implementations, an alert may be generated in response to detecting a change of condition. In some implementations, a recommended course of action may also be generated.

In some implementations, an annotation process may be used to generate labels for audio feature vectors that correspond to potentially relevant sounds in a senior's living space in terms of identifying a senior's condition. In some implementations, caregivers enter the annotations, which may be used to generate labels to identify audio features.

In some implementations, in a learning phase, caregivers are prompted to answer patient condition questionnaires. The questionnaires may be augmented in the sense that they include fields to associate one or more questions, answers, and identified audio features. This may be used to form data to train a machine learning system to automatically complete a questionnaire based on monitored sensor data.

A learning phase may be used to train the machine learning model to passively analyze audio from the senior's living space and automatically determine when various conditions of the senior citizen, have changed. The machine learning system may generate a report or other notification, such as alerts to an appropriate person. A suggested course of action may also be generated to address the detected condition.

In some implementations, during a learning phase, caregivers are prompted to answer the questions of a questionnaire verbally and their responses are used to identify audio features that correspond to specific changes in condition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
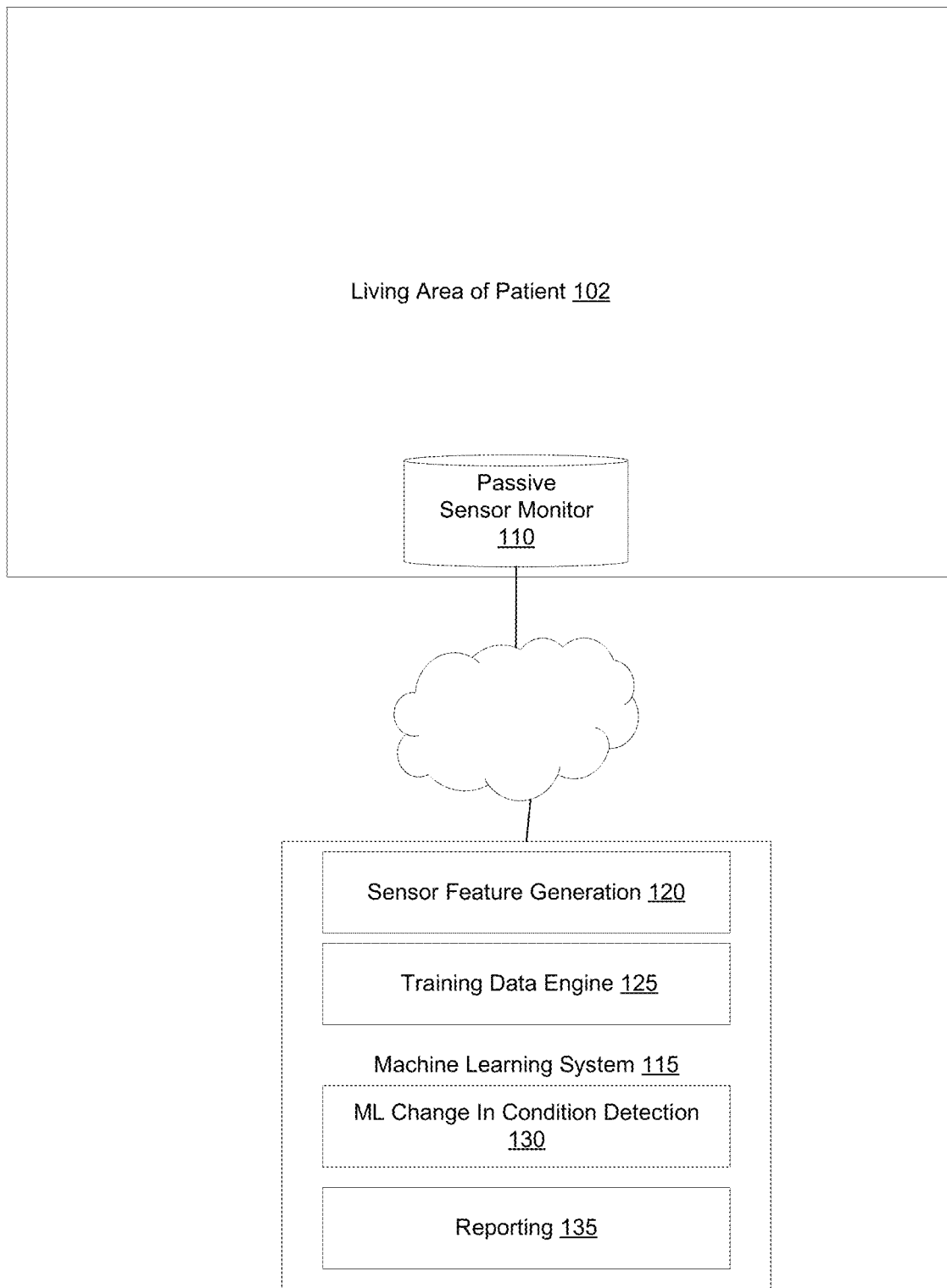
FIG. 1A is a high-level diagram of a machine learning system for detecting a change in a patient condition in accordance with some implementations and FIG. 1B illustrates a server-based implementation of a machine learning system.

FIG. 1A is a high-level diagram of a system in accordance with some implementations. The living area 102 of a patient receiving in-home care (e.g., a senior citizen) has a passive sensor monitor 110. The passive sensor monitor may be an audio monitor, although more generally it could also be one or more other sensor monitors, such as a camera, a video camera, or a motion sensor. In some implementations, the passive sensor monitor is a voice assistant or a video-voice assistant.

Figure 1B:
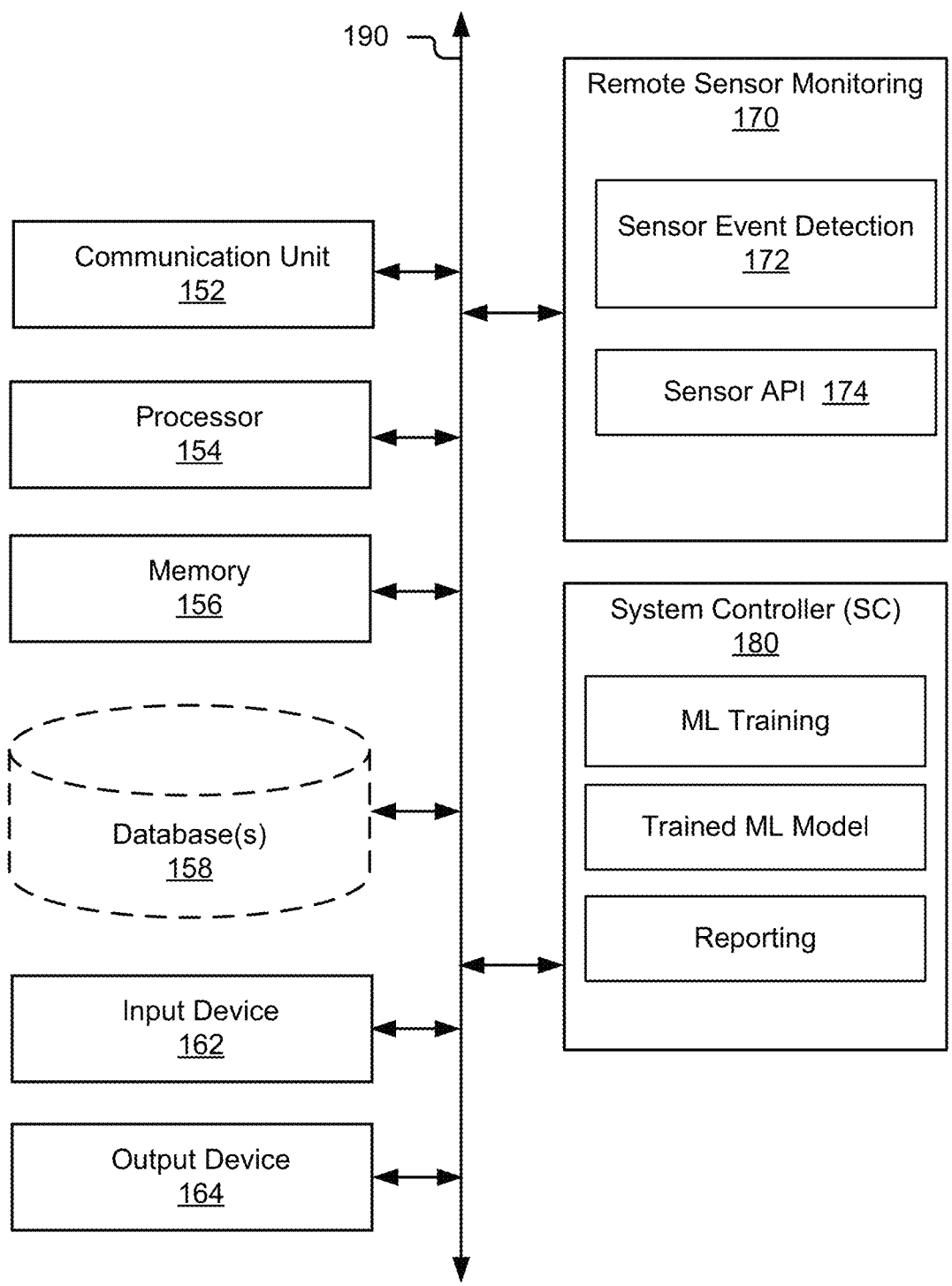

The output of the passive sensor monitor 110 is provided to a machine learning system 115. The machine learning system 115 does not have to be located at the home of the patient. As some examples, it could, for example, be provided as a network-based service or as a cloud-based service. A sensor feature generation engine 120 generates sensor feature vectors from the received sensor data. This may include, for example, extracting sensor features that are relevant to monitoring the health of a patient. For example, background noises (e.g., nearby construction noise) may be filtered out. A training data engine 125 may be provided to generate training data to train a machine learning model to perform condition change detection 130. In some implementations, the machine learning model is trained based on training data that associates sensor feature vectors with questions of a health questionnaire. The trained machine learning model is used to detect a change in condition. When a change in condition is detected, a reporting module 135 may generate a report. The report may, for example, include a notification, an alert, or a recommended follow up action. The machine learning system may, for example, include one or more processors and memory to implement components as computer executable instructions. As one example the machine learning system may be implemented on a server, as illustrated in FIG. 1B. For example, a networked server may include an internal communications bus 190, a network communication unit 152, a processor 154, a memory 156, a database 158, an input device 162, an output device 164, a remote sensor monitoring module 170 to monitor the passive sensor monitor. This may include, for example, a sensor API 174 and sensor event detection 172. A system controller 180 may include a module for ML training, the trained ML model, and reporting. However, many variations in the physical implementation of the machine learning system are possible.

Figure 2:
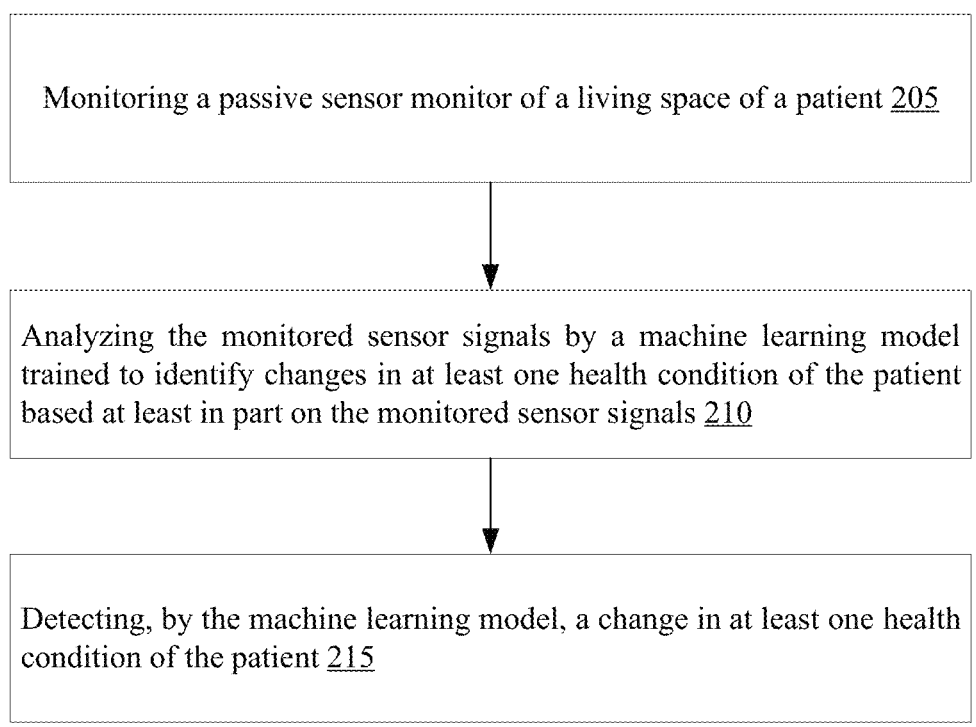
FIG. 2 is a high-level flow chart of a method of detecting a change in condition in accordance with some implementations.

FIG. 2 is a high-level flow chart illustrating a method in accordance with some implementations. In block 205, monitoring is performed by a passive sensor in the living space of a patient. In block 210, the monitored sensor signals are analyzed by a machine learning model trained to identify changes in at least one health condition of a patient. In block 215, a change in at least one health condition of the patient is detected by the trained machine learning model.

Figure 3:
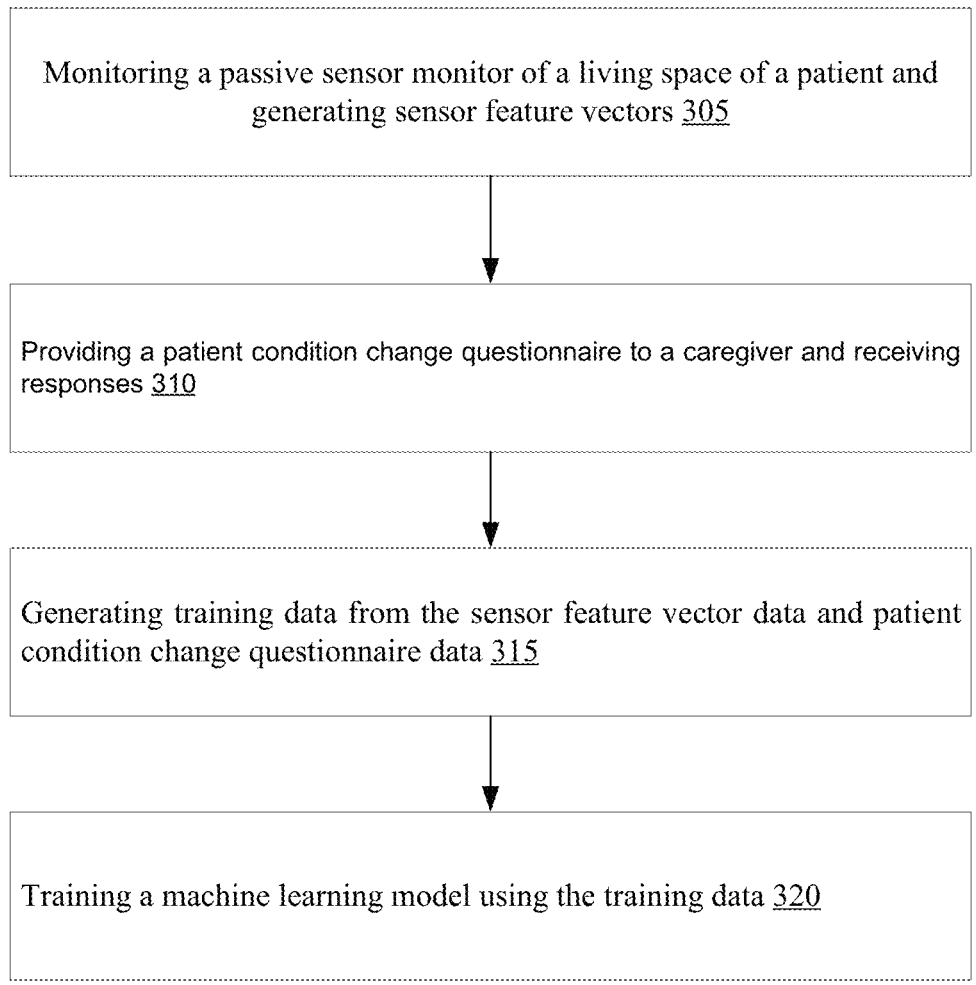
FIG. 3 is a high-level flow chart of a method of generating training data for training a machine learning model in accordance with some implementations.

FIG. 3 is a flow chart illustrating a method of generating training data to train the machine learning model in accordance with some implementations. In block 305, sensor feature vectors are generated based on monitoring an output of a passive sensor monitor of a living space of a patient. In block 310, a caregiver is provided with a patient condition change questionnaire that the caregiver fills out during the learning phase. In block 315, training data is generated based on the sensor feature vector data and patient condition change questionnaire data. In block 320, the training data is used to train the machine learning model.

Figure 4:
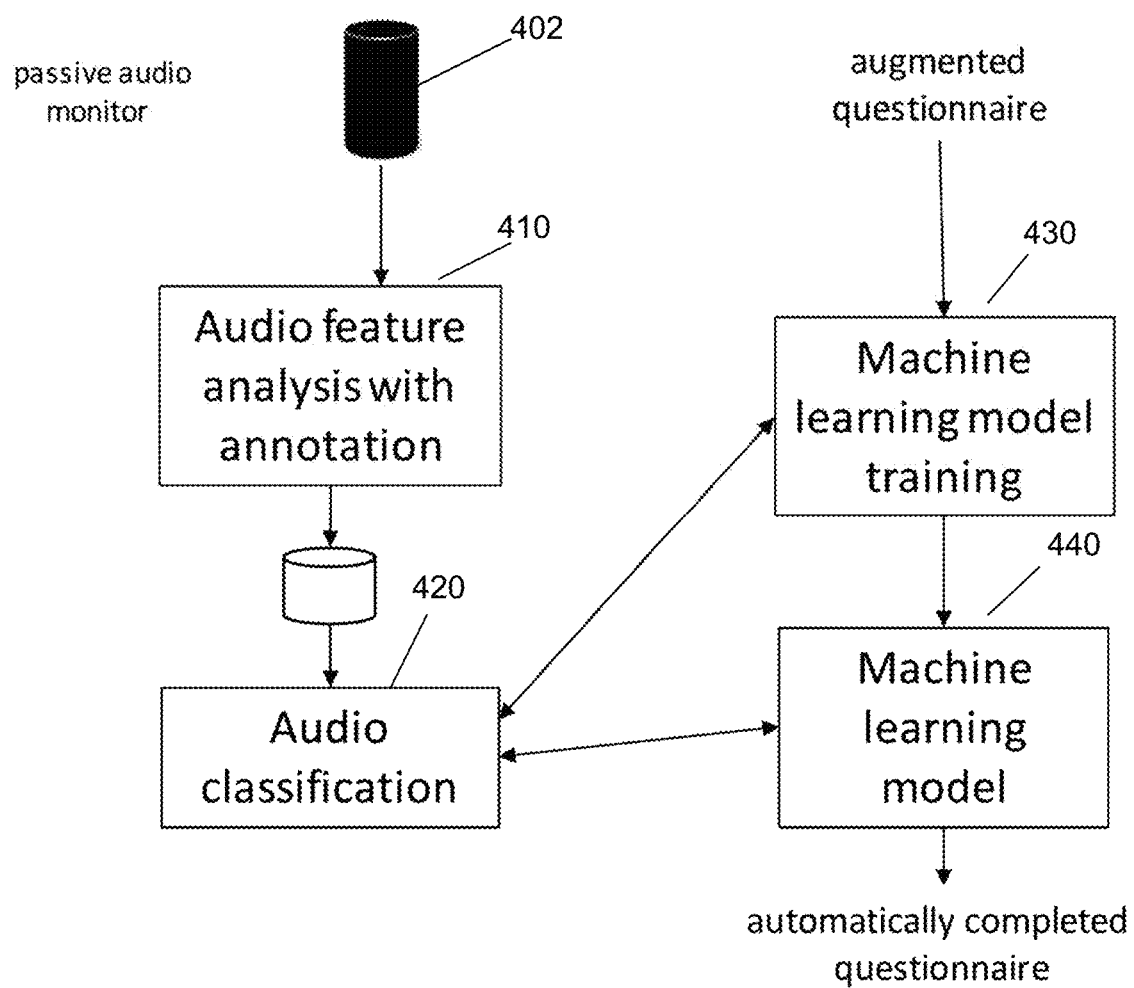
FIG. 4 illustrates a system architecture in accordance with some implementations.

In some implementations, the passive sensor monitor is an audio monitor. FIG. 4 illustrates some aspects of a machine learning system related to training a machine learning system to automatically learn audio feature classification and train a machine learning model to complete diagnostic questionnaires without human input and identify a change in condition.

A passive audio monitor 402 (e.g., Amazon Alexa®) is deployed in a senior citizen's living area to provide data that is input to an audio feature analysis and annotation unit 410. In some implementations a caregiver in charge of caring for a senior enters annotations for particular sound-related events. The annotations may, for example, be entered by a voice command but more generally could be entered in other ways. The annotations are used to generate labels to aid audio classification unit 420 in generating classifications for audio features. For example, in a training phase, a caregiver may enter an annotation when a senior is washing their hands in the bathroom. This thus generates a label that is specific to the types of sounds in the senior's living area for specific events.

In some implementations the audio features (e.g., cepstral coefficients) are analyzed in comparison with short audio clips, classifications for those clips (e.g., running water), and events associated with the clips (e.g., "washing hands in the bathroom"). Audio classification module 420 is given short audio clips and matches audio feature vectors to examples in the database. Augmented questionnaires are input to a machine learning model training module 430 that associates results produced by audio classification with answers to questions provided by a caregiver. The machine learning model 440 (after training is complete) receives input from the audio classification routine and automatically completes a questionnaire without human intervention.

As an illustrative example, the augmented questionnaires may include questions such as "Did the senior slip or fall while you were there?" as well as sounds associated with that event (e.g., falling sounds). The machine learning model training module 430 learns audio features that correspond to question/answer pairs. For example, falling sounds are associated with the YES answers to "Did the senior slip or fall?"

Audio Feature Analysis

Figure 5:
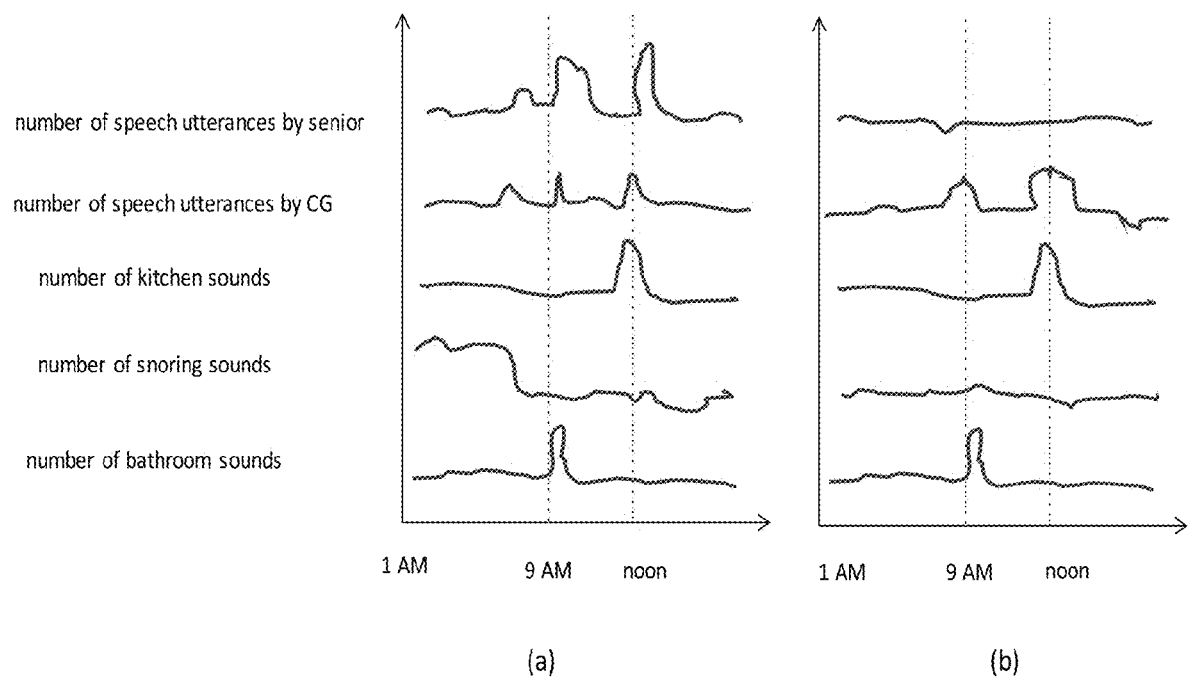
FIG. 5 illustrates two different examples of multivariate time series data for different audio feature vectors in accordance with some implementations.

FIG. 5 shows an example of a multivariate time series data collected from a senior citizen's living space by a passive audio monitoring device from 1 AM to 4 PM on two days one month apart. FIG. 5A illustrates the multivariate time series data collected on a first day and FIG. 5B illustrates the multivariate time series data a month apart. As an example, tracking may be performed of a number of speech utterances over time by the senior and the caregiver (CG), the number of kitchen sounds (e.g., dishes and silverware clanging), the number of snoring sounds, and number of bathroom sounds (water running, flushing, etc.). The labels, e.g. "speech utterances by senior" are provided by a supervised machine learning classifier. The labels could also be cluster identifiers (e.g., $c_1, c_2, \ldots, c_n$) provided by an unsupervised machine learning classifier.

Figure 6:
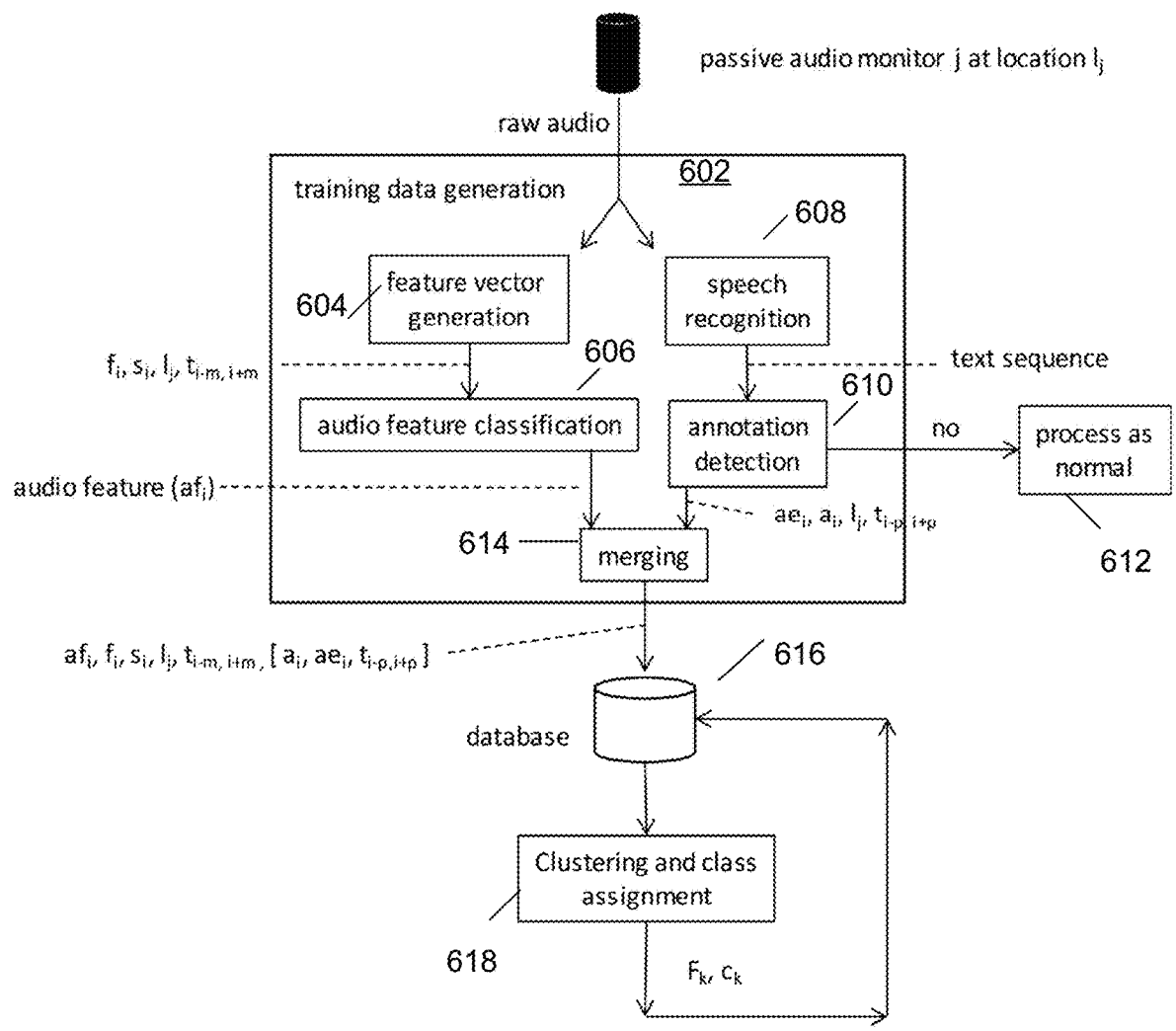
FIG. 6 is a diagram illustrating aspects of audio feature analysis and annotation in accordance with some implementations.

FIG. 6 shows a method for performing audio analysis to generate training data 602 to label feature vectors in accordance with some implementations. Raw audio from a passive listening device is processed in parallel by feature vector generation 604 and speech recognition 608. In one implementation, a feature vector generation 604 process finds the vector of Mel Frequency Cepstral Coefficients (MFCC) $f_i$ for each time window $t_{i-m,\ i+m}$ and tags each vector with the location $l_j$ of the passive audio monitoring device. The audio feature classification 606 routine compares each vector of MFCC coefficients to the MFCC coefficients derived from background noise and known sounds. It outputs identifiers for audio features $af_i$ such as speech utterance by client, sleeping sounds, pain sounds, walking sounds, etc.

The speech recognition 608 path applies speech recognition to the raw audio data to produce a sequence of text. Annotations are detected by first locating trigger phrases in the text (e.g., the phrase "audio event" is a trigger phrase). If a trigger phrase is found, the text following the trigger phrase is matched to the scripts shown in Table 1. If one or more of the words in each group of words in the left column are found, the corresponding audio event (ae) is asserted to have occurred. The merging 614 routine combines the audio feature information ($af_i$, $f_i$, $s_i$, $l_j$, $t_{i-m,i+m}$) with the information derived from speech recognition ($ae_i$, $a_i$, $l_j$, $t_{i-p,i+p}$) and saves both in the database.

For example, if the user says "computer, audio event, senior Martha is washing her hands." Detection of the trigger phrase "audio event" would cause the annotation detection routine to match "senior Martha is washing her hands" to a script, such as the illustrative script shown in Table 1. In the example of Table 1, the first row would match the audio event "bathroom 1", which would be identified from time $t_{i-p}$ to time $t_{i+p}$. If an annotation was not spoken, the speech act is processed as normal. For example, if the user says "computer, what was the score in the Giants game last night?" the system would look up the answer to that question and speak it to the user.

Table 1 shows some of the scripts used for annotation. Each of the words indicated must be present in the text that occurs after the trigger phrase for the event to be associated with the clip. The merging 614 routine tags the feature vectors whose windows overlap with the time interval $t_{i-p}$ to time $t_{i+p}$ with the label assigned by the user (e.g., bathroom event 1).

TABLE 1

Example scripts for annotating audio events.

| Word matches | Audio Event (ae) |
|---|---|
| [wash, washing], [hands, feet, face] | bathroom 1 |
| [washing, doing], [laundry] | laundry 1 |
| [going, making], [poddy, kaka] | bathroom 2 |
| [doing, cleaning], [dishes] | kitchen 1 |
| [running, starting, using], [dishwasher, range] | kitchen 2 |
| [sleeping, napping], [bed, couch, recliner] | sleeping 1 |
| [watching, enjoying], [TV, television] | TV 1 |
| [talking, chatting], [PROPER NAME] | conversation 1 |
| [talking, calling], [phone, cell, telephone] | phone call 1 |
| [phone, cell, telephone], [ringing, buzzing] | phone call 2 |
| [PROPER NAME], [cooking, baking] | kitchen 3 |
| [PROPER NAME] [shaving, brushing teeth] | bathroom 3 |
| [PROPER NAME], [snoring, sleeping, resting] | sleeping 2 |

In one implementation, the feature vector generation 604 process is applied to 25 ms audio frames that are extracted from the input audio every 10 ms (overlapping). The Discrete Fourier Transform (DFT) of the frame is then computed as follows:

$$S_i(k) = \sum_{n=1}^{N} s_i(n) h(n) e^{-j 2\pi k n / N} \quad 1 \le k \le K$$

where h(n) is an N sample long analysis window and K is the length of the DFT.

The periodogram estimate of the power spectrum is then computed:

$$P_i(k) = \frac{1}{N} |S_i(k)|^2$$

The absolute value of the complex Fourier transform is taken and result squared. A 512 point fast Fourier transform (FFT) is performed and the first 257 coefficients are kept.

The energy in 26 Mel-spaced filterbanks is calculated by multiplying 26 triangular filters, each of which is tuned for a particular frequency range, with the periodogram power spectral estimate. This gives 26 numbers that represent the amount of energy present in each filterbank. The discrete cosine transform (DCT) of the log of the 26 energy values is taken and the first 12 coefficients retained. These are the MFCC coefficients. A feature vector is generated by concatenating the MFCC coefficients for the frames in an audio clip. For example, a five second (5000 ms) audio clip would produce a feature vector with 500*12=6000 features, assuming the standard 10 ms overlap.

Figure 7A:
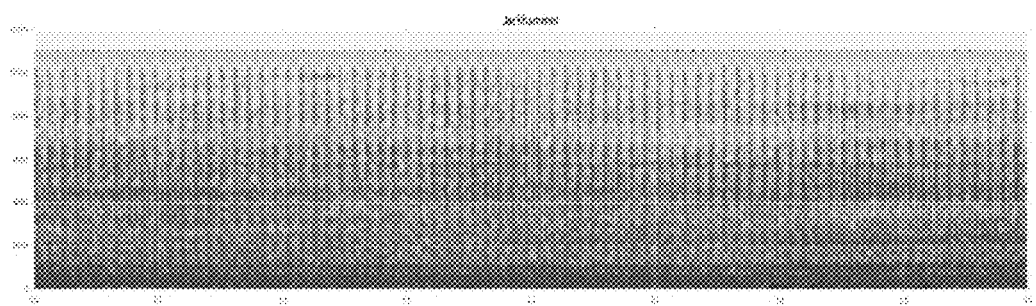
FIGS. 7A and 7B illustrates example spectrograms for a Jack Hammer (top) and an air conditioner (bottom).
Figure 7B:
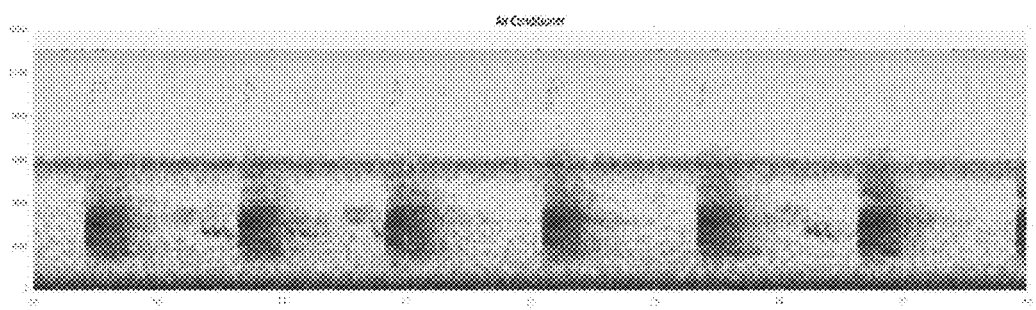

Feature detection also includes calculation of the spectrogram $s_i$ for each 25 ms audio frame. The spectrogram is comprised of multiple FFTs, one for each audio frame. The X axis is time and the Y axis is the magnitude of the frequency components. FIGS. 7A and 7B shows example spectrograms for X and Y. The dominant frequencies are significantly different in the two clips. The spectrogram is computed given x=(x1, . . . , xt) that denotes a segment of an audio signal of length t, as:

$$s_i = s_k(x) = \left| \sum_{s=1}^{t} e^{iks} x_s \right|^2 = \left( \sum_{s=1}^{t} \cos(ks) x_s \right)^2 + \left( \sum_{s=1}^{t} \sin(ks) x_s \right)^2$$

where k is the window size (number of samples) over which the FFT is calculated. We have found the 1024 samples from a 25 ms audio signal sampled at 44100 Hz provide the best performance.

FIGS. 7A and 7B demonstrates the ability of the spectrogram to represent noises in the environment. For example, FIG. 7A shows the spectrogram for a jackhammer. There are high amplitudes across all frequencies repeated at the rate of operation of the jackhammer. FIG. 7B shows the spectrogram for an air conditioner. There is a dominant frequency at about 6 kHz (the dark band across the middle of the image) and repeated dark bands over a range of lower frequencies. These correspond to the rumbling of the compressor.

Figure 8:
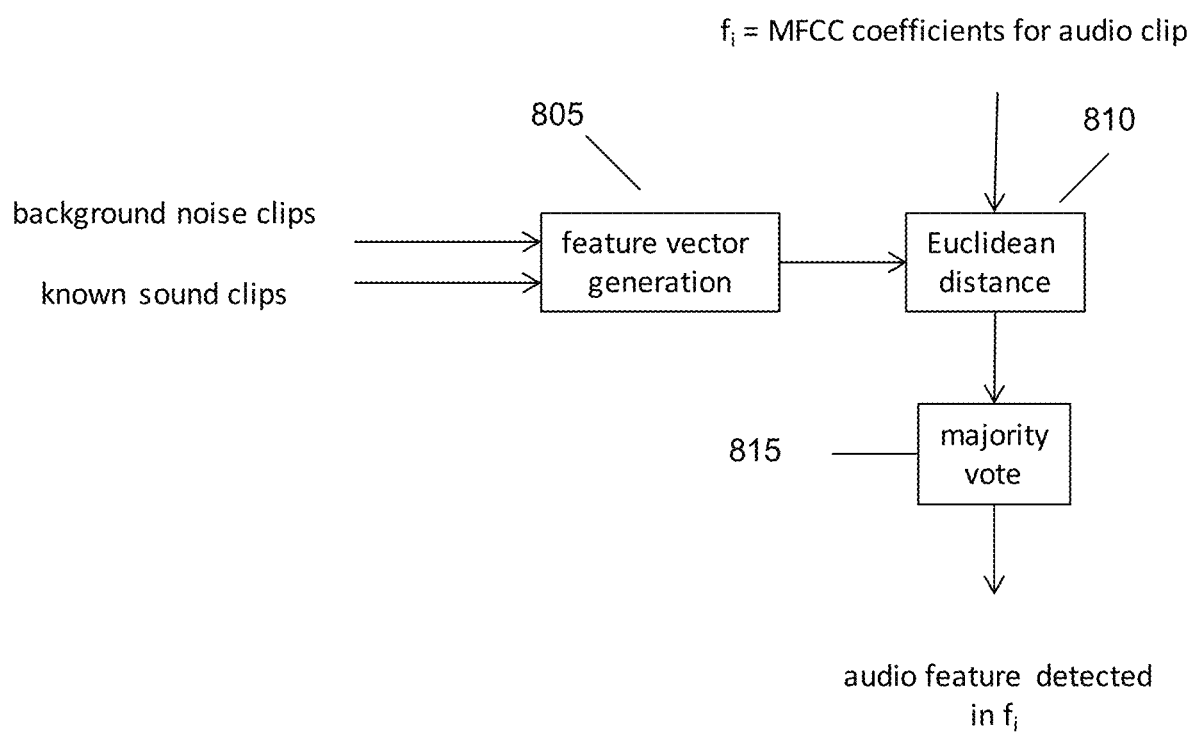
FIG. 8 is a diagram illustrating audio feature classification in accordance with some implementations.

FIG. 8 shows a technique for audio feature classification in accordance with some implementations. A set of background noise clips are obtained from each passive audio monitor. As an example, audio monitoring of the living space may be performed when no one is present and sampling 5 second clips is performed every 10 minutes for 24 hours. If this is not possible because the living space is always occupied, the audio clips are manually sampled while asking everyone to be quiet while a 5 second audio clip is captured. This is typically done ten to twenty times for each passive audio monitor. A set of known sound clips are obtained from a set of previously annotated audio clips, captured as described earlier either in this senior's living space or in other seniors' living spaces. Known sound clips can also be obtained from publicly available sources such as the Urban Sound Dataset described in J. Salamon, C. Jacoby and J. P. Bello, "A Dataset and Taxonomy for Urban Sound Research", 22nd ACM International Conference on Multimedia, Orlando USA, November 2014, the contents of which are hereby incorporated by reference.

If not previously performed, the feature generation 805 process described above is applied to each of the background noise clips and known sound clips. The Euclidean distance 810 between the MFCC coefficients is computed for each frame in $f_i$ and the MFCC coefficients for each frame in the background noise and known sound clips. The clip with the frame that most closely matches the frame in $f_i$ votes for that class (background or known sound). This operation is performed for all the frames in $f_i$ and accumulate the votes for each class. If known sound clips receive the majority vote 815, the algorithm decides that an audio event has been detected. For example, a 5 second audio clip would yield 500 votes, assuming a standard 10 ms overlap value. If the known sound category received more than 250 votes, we decide that an event was detected. Alternatives to the Euclidean distance classifier include support vector machines or deep learning.

The merging 614 process in FIG. 6 combines audio feature vectors $af_i$ with audio event vectors $ae_i$ when their time spans overlap. As the system runs, it accumulates a database of audio feature vectors, the classifications associated with them such as speech utterances by the client, agitated speech, pain sounds, etc, and the labels that are the result of annotation (e.g., bathroom, laundry, kitchen events, etc.). Audio feature vectors can also be labelled as an unknown audio event or background noise.

The clustering and class assignment 618 routine in FIG. 6 applies a hierarchical agglomerative clustering algorithm to produce a set of feature vectors $F_k$ and labels $c_k$. The feature vectors are averages and standard deviations of the cepstral coefficients of the samples in the corresponding cluster. The labels are either synthetically generated if unsupervised learning is used or they are the annotations applied by the user, as described above. The feature vectors in a cluster represent similar sounds that might have occurred in different locations. For example, speech utterances, pain sounds, walking sounds, etc. Clustering also uses the results of annotation detection to determine the location and type of activity that occurred when the audio was recorded. For example, the sounds produced by washing hands associated with the label "bathroom 1" tells us that this was a bathroom sound. The sounds produced by washing dishes associated with the label "kitchen 1" tell us that this was a kitchen sound.

Machine Learning Training and Model Application

Augmented Questionnaire

Table 2 shows an example of an augmented questionnaire, although more generally the questionnaire may include a different selection of questions and associated audio features. The questionnaire is augmented in that it has additional fields not found in a conventional health questionnaire, such as fields for audio features. In some implementations, it includes a set of passive keywords. In one implementation, each question can be answered either Yes or No. In some implementations, here are primary and follow-up questions. When a positive response is received to a primary question, the corresponding follow-up questions are asked to clarify the report. "Passive" keywords are also shown that can indicate the corresponding question when the speech-to-text system detects them in the audio stream. Features that can exist in the audio stream are also listed that can corroborate the existence of the condition indicated by the question. For example, when the question "Does the client show any signs of pain?" is asked, the system expects to hear pain sounds in the audio stream.

TABLE 2

Augmented questionnaire for change in condition monitoring.

| Primary (P) or Follow-up (F) question | question | passive keywords | audio features |
| --- | --- | --- | --- |
| P | Does the client seem different than usual? | different, changed | all features |
| F | Does the client show any reduced talking or alertness? | talkative, talking | speech utterances by client |
| F | Is the client newly agitated, confused, or sleepy? | agitated, angry, confused | speech agitation of client, speech utterances by client, sleeping sounds, sleeping location |
| F | Does the client show any signs of pain? | pain | pain sounds |
| P | Has there been a change in mobility? | moving, mobile | walking sounds by client |
| F | Has there been a change in the ability to stand or walk? | standing, walking | walking sounds by client |
| F | Has there been an observed or unobserved fall or slip? | fall, slip | falling sounds |
| P | Has there been a change in eating or drinking? | eating, drinking | kitchen sounds |
| P | Has there been a change in toileting? | toileting | bathroom sounds |
| F | Has there been any discomfort, smell or change in frequency associated with urination? | urination | bathroom sounds |
| F | Has the client had diarrhea or constipation? | diarrhea, constipation | bathroom sounds |

TABLE 2-continued

Augmented questionnaire for change in condition monitoring.

| Primary (P) or Follow-up (F) question | question | passive keywords | audio features |
|---|---|---|---|
| P | Has there been a change in skin condition or increase in swelling? | skin, swelling | pain sounds |
| F | Have there been any new skin rashes or wounds | rash, wound | pain sounds |

The questionnaire thus may include a number of different questions regarding individual changes in condition. However, it will also be understood that the interpretation of a combination of answers to individual questions may be important in determining a likely significance of a change in condition and an urgency in regards to generate a notification or alert of a change in condition. For example, a combination of changes may correspond to an overall change in condition for which it may be prudent to generate an alert or recommend a follow up action such as contacting a nurse to check-in on the patient, contacting the patient's doctor, etc.

Figure 9:
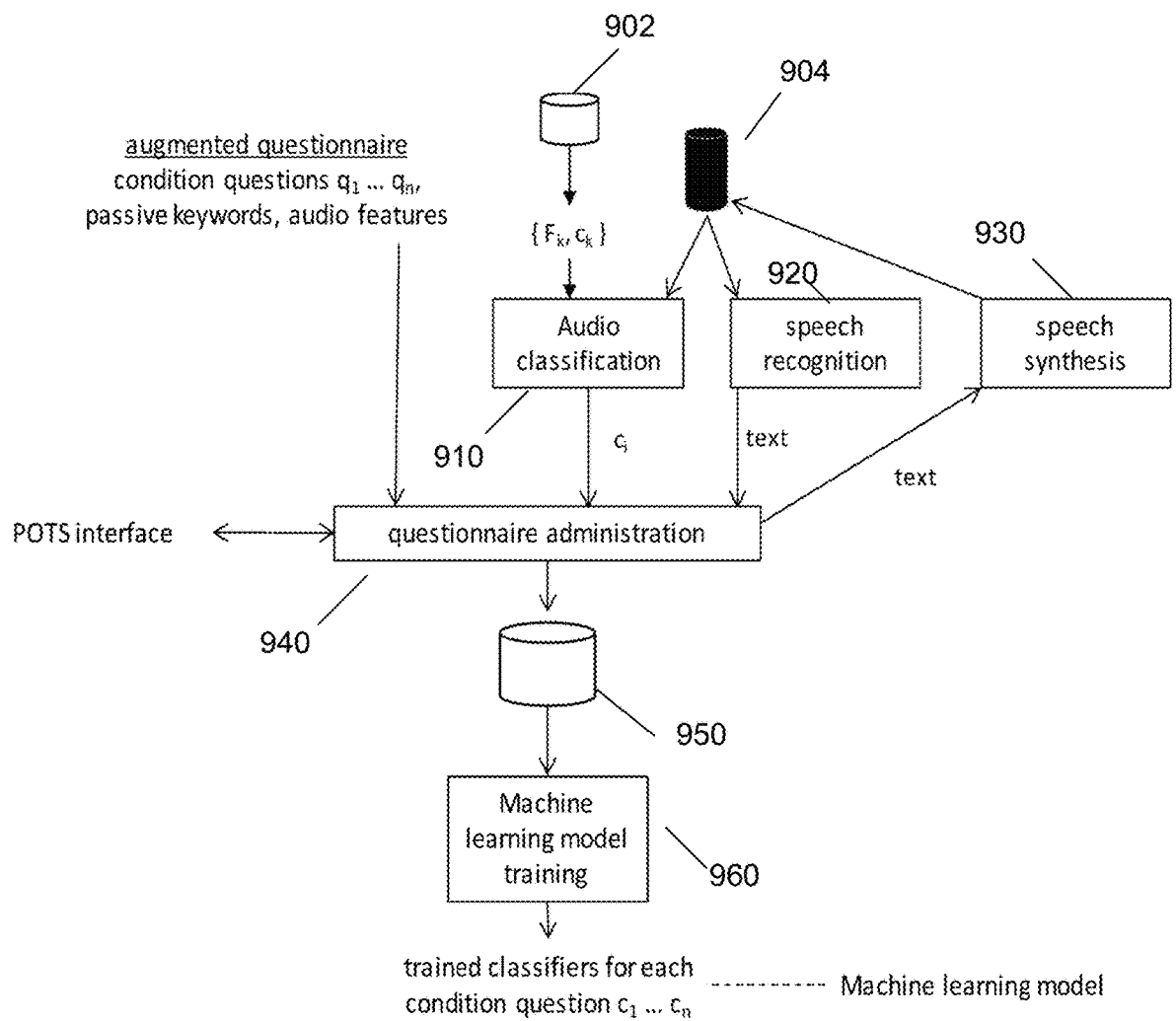
FIG. 9 is a diagram illustrating questionnaire administration and machine learning model training in accordance with some implementations.

FIG. 9 shows an architecture for administering augmented questionnaires and training machine learning classifiers that automatically detects changes in condition in accordance with some implementations. Audio classification 910 and speech recognition 920 are applied continuously to audio 904 that's passively captured in a patient's living space, as described with respect to FIG. 4. The audio classification 910 identifies features in the augmented questionnaire. Speech recognition 920 identifies passive keywords in the augmented questionnaire. Speech synthesis 930 is used to ask a caregiver questions from the augmented questionnaire and is used to verify the existence of a change in condition when passive keywords are identified. The questionnaire administration module 940 asks questions and records answers at the end of each caregiver's shift either using speech synthesis plus recognition, or over a conventional telephone with a plain old telephone service (POTS) interface. Those results, plus the audio features 902 and record of any dialog with the caregivers, are stored in the system database 950. After enough data has been accumulated, machine learning classifiers are trained 960 for each question in the augmented questionnaire.

Figure 10:
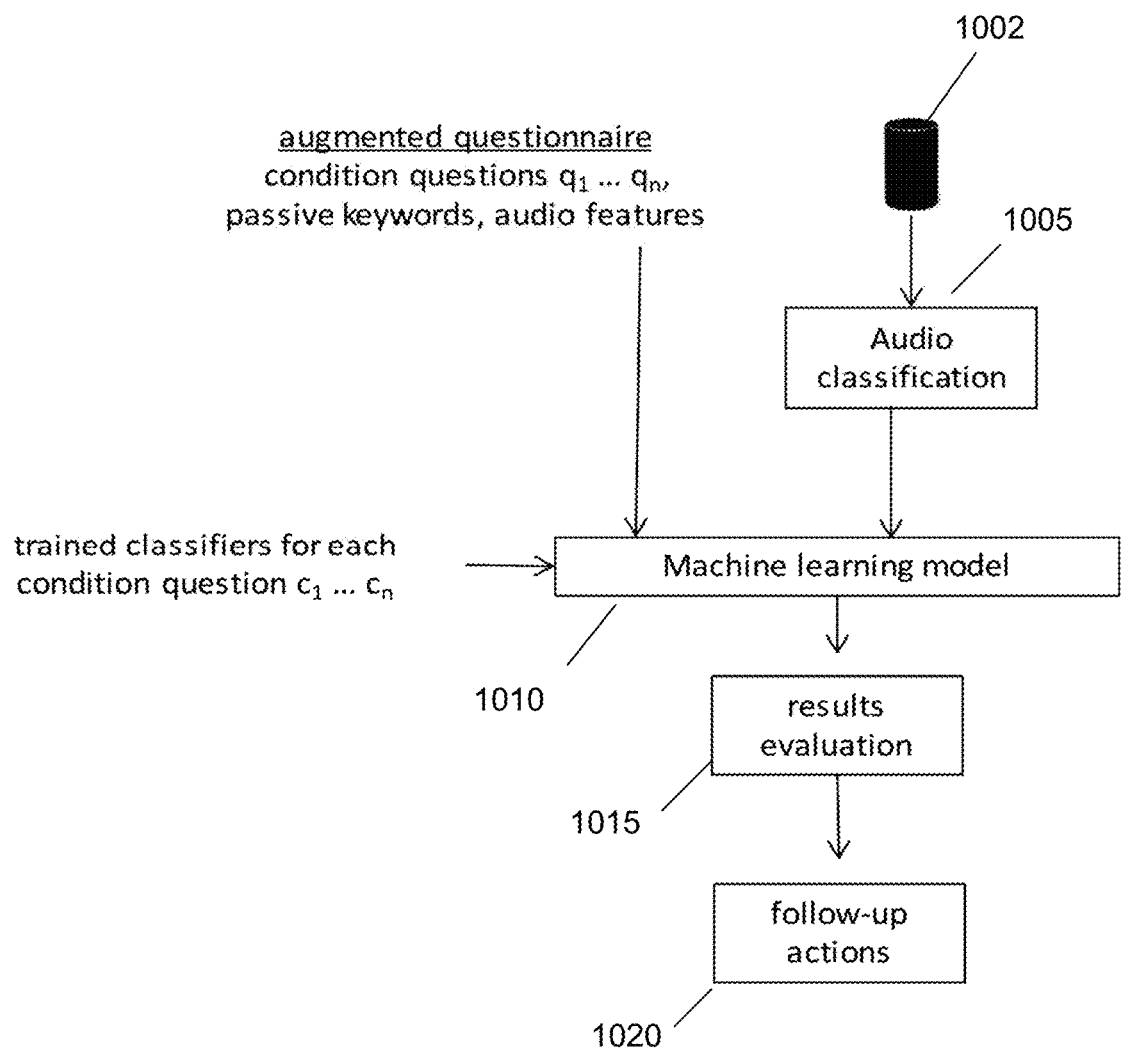
FIG. 10 is a diagram illustrating automatic questionnaire completion in accordance with some implementations.

FIG. 10 shows an architecture for automatically completing an augmented questionnaire in accordance with some implementations. Audio classification 1005 is continuously applied to the stream of audio 1002 passively captured in a client's living space. The trained classifiers developed in FIG. 9 are applied in a machine learning model 1010 to those features and the results are evaluated to determine whether a patient's condition has changed. Follow-up actions 1020 are triggered as required.

An example of applying the technique described in FIGS. 9 and 10 concerns the question "Has there been a change in the client's eating or drinking?" During the training phase kitchen sounds are continuously detected. According to the augmented questionnaire, a change in eating or drinking would be indicated by a change in kitchen sounds. If a caregiver is present when a change is observed, she might say "Martha, why did you stop eating today?" Because of the presence of the passive keyword "eating" in this question, the questionnaire administration module would trigger a confirmation prompt "Caregiver Cathy, did you observe a change in the client's eating or drinking?" Cathy's response would be obtained from the speech recognition module and stored together with the recent kitchen sound features as well as the kitchen sound features from several days ago when the client was eating normally. These features would be used to train a two-class logistic regression classifier that determines whether there has been a change in the client's eating or drinking. Follow-up actions in this case would include the dispatching of a caregiver or a care manager to determine why the client's eating or drinking changed and what should be done to remedy the situation.

Additional Sensing Modalities

Figure 11:
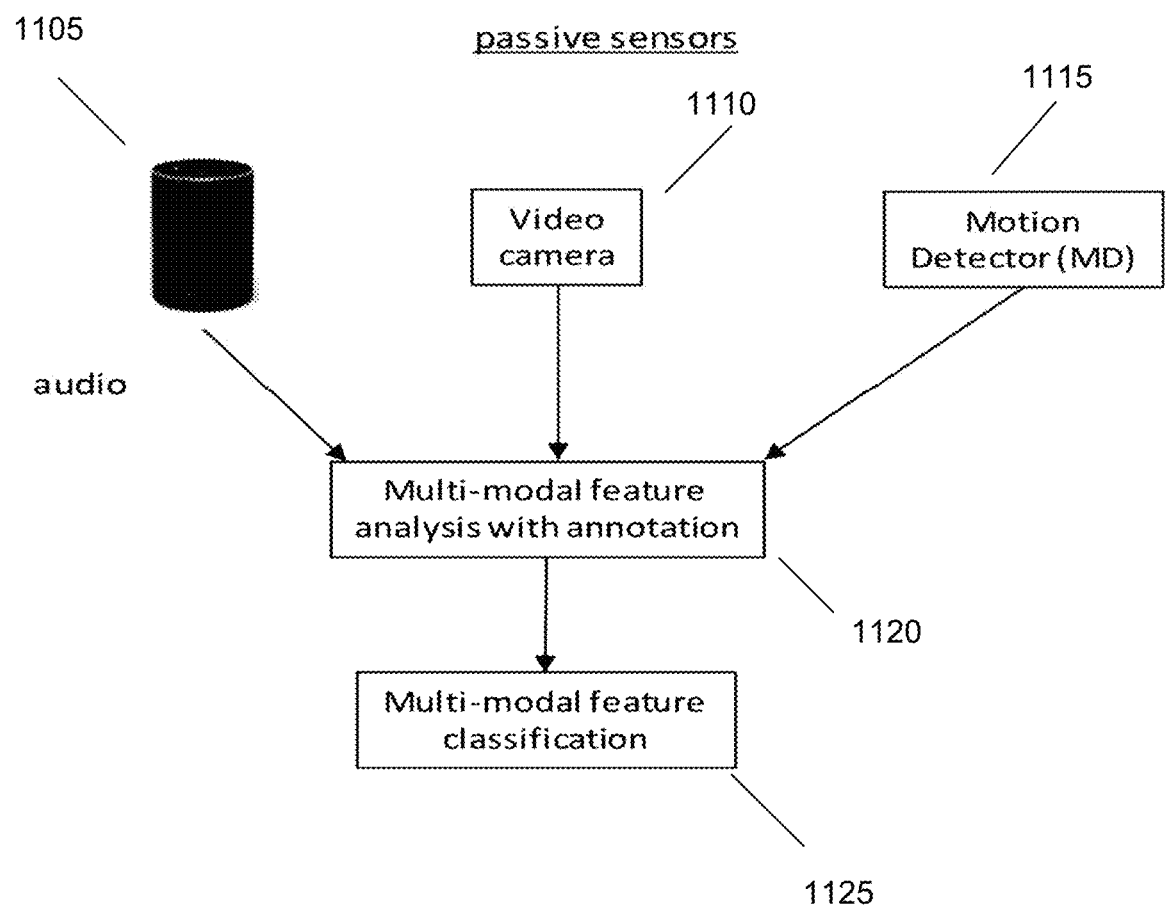
FIG. 11 is a diagram illustrating multimodal feature classification in accordance with some implementations.

FIG. 11 shows the addition of several passive capture sensors in addition to audio in some implementations. The previously described system architecture readily accommodates additional sensors with a substitution of multimodal feature analysis and classification routines for the previously described audio feature analysis and classification. The rest of the architecture (classification, etc.) remains the same. The only difference is that a composite feature vector is built that incorporates features for each modality. For example, in addition to the cepstral coefficients used for each audio frame of an audio monitor 1105, we add 24 Fourier spectrum features for the video camera 1110 and a count of the number of activations produced by the motion detector 1115. (See, e.g., A. Davix, J. Moses, S. Pittala, E. Chaitanya, "Fourier Spectrum Features For Face Recognition", Int. Journal of Innovative Technology and Exploring Engineering (IJI-TEE), ISSN: 2278-3075, V. 9 issue 7, February 2020, the contents of which are hereby incorporated by reference). The composite feature vector is processed in the same way as the original audio feature vector is processed in FIG. 6. The audio feature classification routine in FIG. 5, now called Multimodal Feature Classification 1120, uses background video, known video (e.g., caregiver walking past the camera), and motion detector output from background and known events. Euclidean distance is still used as the multimodal classification algorithm.

Questionnaire Customization

Figure 12:
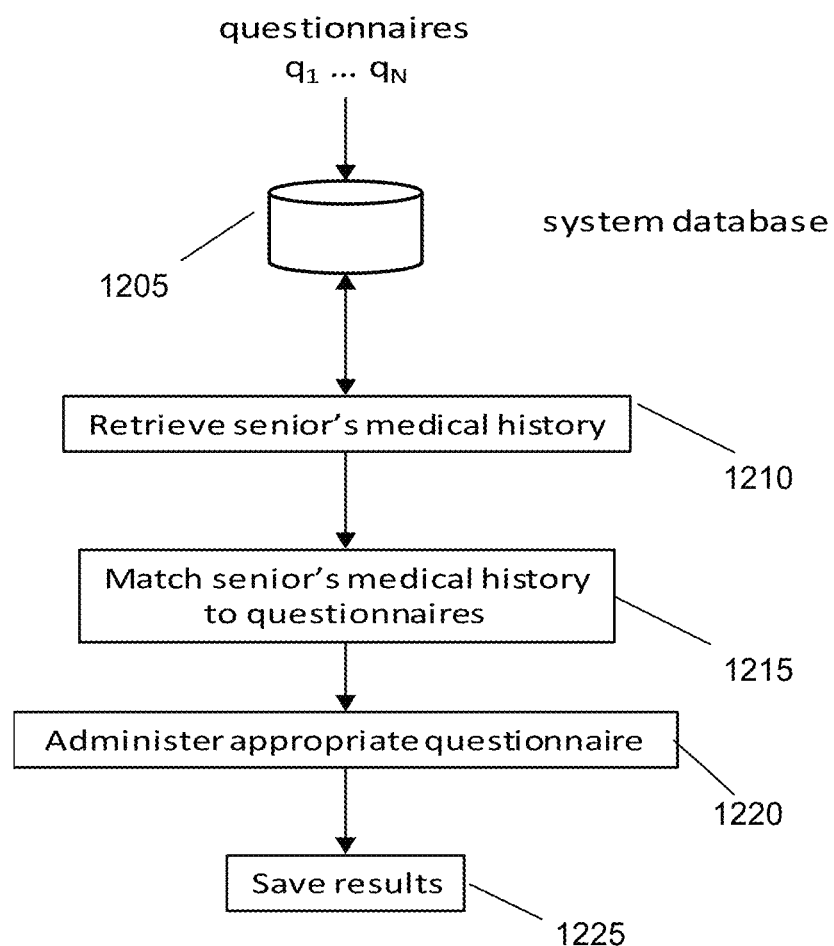
FIG. 12 is a flow diagram illustrating questionnaire customization in accordance with some implementations.

The questionnaires administered to patients, first manually by caregivers and then automatically by the proposed system, can be customized based on the predicted disease trajectory of the senior. FIG. 12 shows an example of this concept. Questionnaires for given disease trajectories are stored in the system database 1205 and retrieved. One example is the progression of diabetes. At the early stage a senior will have an elevated fasting insulin level and A1C in the normal range. This is the metabolic state prior to pre-diabetes. The questionnaire for this type of senior would include questions related to potential changes in the pre-diabetes condition. The follow-up actions could also be selected based on the pre-diabetes condition. For example, the customized questionnaires in this example could ask about the amount of sugary foods they eat. Follow-up actions could include email suggestions about sugar substitutes. At a later stage A1C would be slightly elevated, in the pre-diabetic range. Questions would include "How much bread and pasta are you eating?" and "Has your weight increased in the last month?" Follow-up actions would include a visit by a dietician. Later, if the dietary interventions are not effective, the senior would become type 2 diabetic. Questions would then focus on health effects such as blurry vision, sores that don't heal, etc. Follow-up actions would include visits by a nurse if personal attention is indicated.

More generally the customization of the questionnaire could be for other medical conditions besides diabetes.

The collection of questionnaires $q_1 \ldots q_N$ shown in FIG. 12 is matched 1215 to a senior's medical history and the questionnaire that most closely matches is administered to the senior as indicated by the training process in FIG. 12 and the completion process in FIG. 10. The matching process uses the senior's medical history 1210. In the example of a senior who's susceptible to diabetes, we use the senior's fasting insulin level and A1C score to determine where they are on the continuum of being diabetic and where they are trending. A decision is made to choose and administer 1220 a questionnaire that's precisely tuned to have the maximum effect on the senior's health based on where they are on the continuum. The results of the customized questionnaire is saved 1225. In our example of diabetes, if the senior is pre-diabetic, it's well known that the disease can be controlled and some metabolic damage reversed if the proper dietary intervention is applied (i.e., a low carb diet). The system automatically detects the senior's risky dietary behavior and dispatches a dietician, without the need for on-site medical evaluation, thus potentially reducing long term damage to the senior's health and lowering costs for the insurance company.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

To ease description, some elements of the system and/or the methods are referred to using the labels first, second, third, etc. These labels are intended to help to distinguish the elements but do not necessarily imply any particular order or ranking unless indicated otherwise.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Furthermore, the technology can take the form of a computer program object accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and Modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), Web-Socket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats.

Furthermore, the modules, routines, features, attributes, methodologies and other aspects of the disclosure can be implemented as software, hardware, firmware, or any combination of the foregoing. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment.

What is claimed is:

1. A method comprising:
    monitoring an output of a passive sensor monitor of a living space of a patient;
    providing the monitored sensor output to a machine learning system having a machine learning model including one or more classifiers trained to identify changes in at least one health condition of the patient based at least in part on the monitored sensor output including an audio output, wherein the one or more classifiers are trained by a questionnaire, answered by a caregiver of the patient, having a set of condition questions associated with one or more audio features of the audio output of the monitored sensor output; and
    detecting, by the machine learning system, a change in at least one health condition of the patient based at least in part on an audio feature classification of the audio output.

2. The method of claim 1, further comprising generating an alert in response to detecting the change in at least one health condition of the patient.

3. The method of claim 1, further comprising generating at least one follow-up action in response to detecting the change in at least one health condition of the patient.

4. A method comprising:
    in a training phase, monitoring an output of a passive audio monitor of a living space of a patient;
    generating labels specific to the types of sounds in a patient's living area by having a caregiver answer a health questionnaire to associate particular types of sounds in the patient's living area with specific health condition events;
    training, based at least in part on the generated labels, a machine learning classification model to generate a trained machine model, the trained machine learning model automatically determining answers to a health condition questionnaire based on audio feature vectors in the patient's living area;
    in a deployment phase, monitoring an output of a passive audio monitor of a living space of a patient;
    generating audio feature vectors from the monitored output, classifying the audio feature vectors, and generating an input for the trained machine learning model of a machine learning system to identify changes in at least one health condition of the patient; and
    detecting, by the machine learning system, a change in at least one health condition of the patient.

5. The method of claim 4, wherein the trained machine learning model includes at least one classifier trained to identify patient condition questions.

6. The method of claim 4, further comprising generating an alert in response to detecting the change in at least one health condition of the patient.

7. The method of claim 4, further comprising generating at least one follow-up action in response to detecting the change in at least one health condition of the patient.

8. The method of claim 4, wherein the trained machine learning model is trained, based at least in part on a medical history of the patient, to identify changes in at least one health condition of the patient.

9. A method, comprising:
    monitoring a passive audio monitor of a living space of a patient;
    providing a patient condition change questionnaire to a caregiver to enter annotations for particular sound-related events in the living space of the patient indicative of patient condition change and receiving responses;
    generating training data from the patient condition change questionnaire and audio feature data generated from monitored audio data; and
    training a machine learning model to detect a change in at least one health condition of the patient from audio feature data generated from monitored audio data.

10. The method of claim 9, further comprising customizing at least one question of the patient condition change questionnaire based on a medical history of the patient.

11. A method, comprising:
    training a machine learning model to automatically identify a change in condition of a patient based at least in part on monitored audio data from a living area of patient and information provided by a caregiver, wherein the training comprises using training data generated from monitored audio data and responses of a caregiver to a questionnaire; and
    using the trained machine learning model to detect a change in condition of the patient based on monitored audio data from the living area of the patient.

* * * * *